United States Patent
Ryden et al.

[11] Patent Number: 6,038,707
[45] Date of Patent: *Mar. 21, 2000

[54] SPORTS GOGGLE HAVING A VENTILATING FAN

[75] Inventors: William Dennis Ryden, Colorado Springs, Colo.; Joseph Ross McNeal, Hailey, Id.

[73] Assignee: Smith Sport Optics, Ketchum, Id.

[*] Notice: This patent is subject to a terminal disclaimer.

[21] Appl. No.: 09/012,949

[22] Filed: Jan. 23, 1998

[51] Int. Cl.$^7$ .................................................. A61F 9/02
[52] U.S. Cl. ................................................................ 2/436
[58] Field of Search .......................... 2/436, 437, 171.3, 2/435; 415/214.1, 220; 417/423.15, 234

[56] References Cited

U.S. PATENT DOCUMENTS

| | | |
|---|---|---|
| 3,377,626 | 4/1968 | Smith . |
| 3,691,565 | 9/1972 | Galonek ..................................... 2/14 H |
| 3,825,953 | 7/1974 | Hunter ....................................... 2/14 K |
| 4,150,443 | 4/1979 | McNeilly ..................................... 2/436 |
| 4,309,774 | 1/1982 | Guzowski ...................................... 2/8 |
| 4,443,893 | 4/1984 | Yamamoto ................................... 2/436 |
| 5,031,237 | 7/1991 | Honrud ......................................... 2/8 |
| 5,123,114 | 6/1992 | Desanti ......................................... 2/8 |
| 5,542,130 | 8/1996 | Grabos, Jr. et al. ......................... 2/436 |
| 5,542,480 | 8/1996 | Ryden ......................................... 2/436 |

OTHER PUBLICATIONS

IBM Intell. Prop. Network, Coreless Motor US 5780947, p. 1 of 3, Jul. 26, 1999.

*Primary Examiner*—Diana Oleksa
*Assistant Examiner*—Katherine Moran
*Attorney, Agent, or Firm*—Dale B. Halling

[57] ABSTRACT

A sports goggle (10) has a lens subframe (14) attached to a face subframe (16) by spacer struts (18). The spacer struts (18) form a top open portion (20) and a pair of cheek open portions (22). The face subframe (16) has a face flange (26) conforming to a user's face. The face flange (26) has a trapezoidal opening (28) in a forehead portion and a pair of locking holes (30) on either side of the trapezoidal opening (28).

11 Claims, 2 Drawing Sheets

SPORTS GOGGLE HAVING A VENTILATING FAN

FIELD OF THE INVENTION

The present invention relates generally to the field of sports goggles and more particularly a sports goggle having a ventilating fan.

BACKGROUND OF THE INVENTION

Sports goggles have been used to protect the user from foreign objects, sun and wind. One problem that has occurred with sports goggles is that the have a tendency to fog. Many types of sports goggles attempt to avoid this by having air vents that allow cooler, drier air to circulate through the enclosed space of the goggle. The cooler, drier air lowers the dew point of the air inside the goggle and eliminates the fog. Unfortunately, the air vents help most while the user is moving and provide very little relief once the user has stopped moving. In addition, while the user is moving the lens temperature is lowered. Because the lens temperature is lowered while the user is moving, the lens is more likely to fog over when the user stops moving.

Some manufactures of sports goggles have added circulating or ventilating fans in the top of their sports goggles. These fans have required extensive redesign of the top portion of the sports goggles and generally only fit one style of sports goggles. In addition, the fans are held in place by rigid plastic parts that reduce the flexibility of the sports goggles. This makes the sports goggles less comfortable. In addition, the fans are noisy and have not always eliminated the problem of fogging.

Thus there exists a need for a sports goggle with a ventilating fan that can fit more than one style of goggles, is flexible, quiet and virtually eliminates fogging.

DETAILED DESCRIPTION OF THE DRAWINGS

The invention describes a sports goggle and ventilating fan that has a flexible housing and works with a wide variety of sports goggles. The sports goggle according to the invention includes a lens subframe attached to a face subframe by spacer struts. A ventilating fan assembly having a pair of flexible face flange struts attaches to a forehead portion of the face flange. The ventilating fan assembly is designed to push air through a fan exhaust vent in a top brim of the sports goggle. The use of flexible struts results in both a flexible structure and a structure that can be easily adapted to a variety of sport goggle styles.

Figure 1:
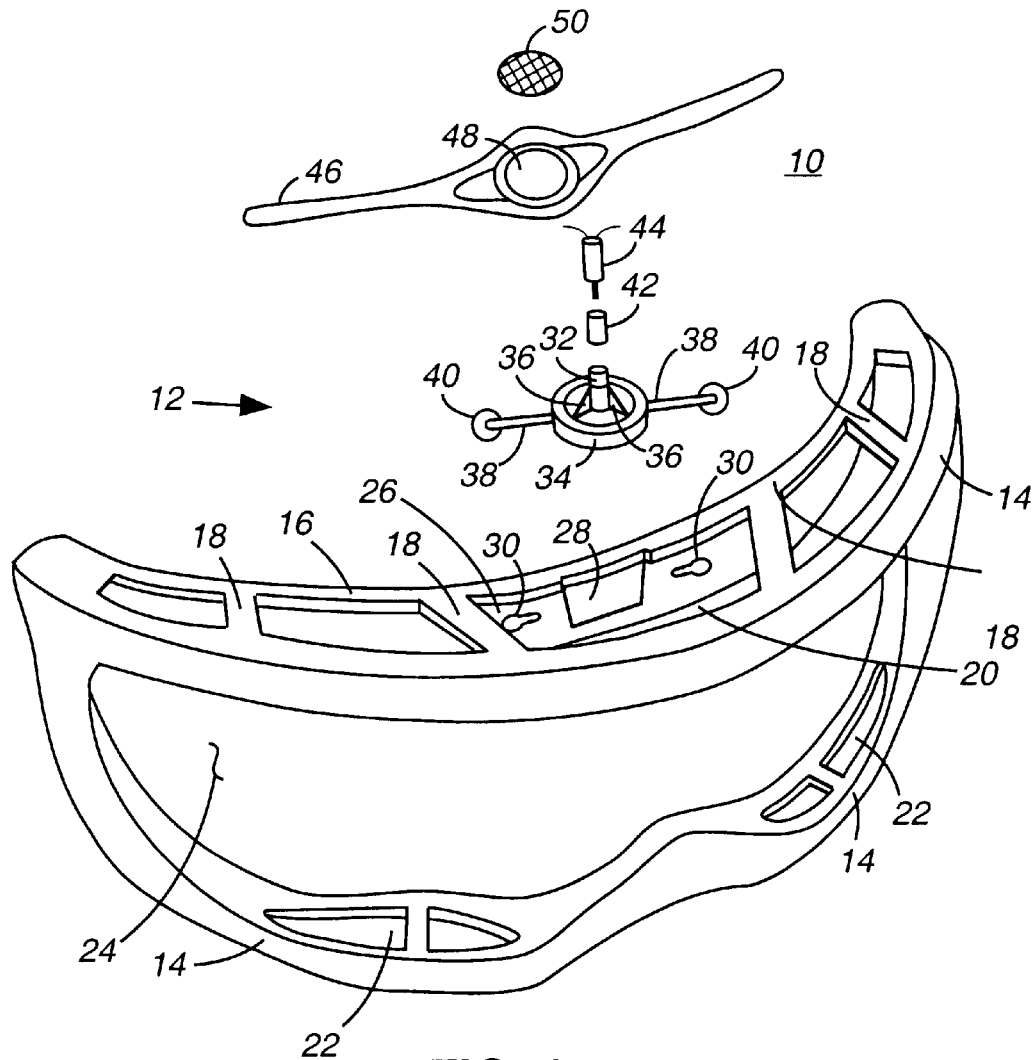
FIG. 1 is an exploded view of an embodiment of a sports goggle having a ventilating fan according to the invention.

FIG. 1 is an exploded view of an embodiment of a sports goggle 10 having a ventilating fan (ventilating fan assembly) 12 according to the invention. The sports goggle 10 includes a lens subframe 14 connected to a face subframe 16 by a plurality of spacer struts 18. The spacer struts 18 form a top open portion (top brim) 20 and a pair of cheek open portions 22. A lens 24 fits in the lens subframe 14. The face subframe 16 has a face flange 26 that conforms to a user's face. The face flange 26 has a trapezoidal opening 28 in a forehead portion of the face flange 26. A pair of locking holes 30 are located on either side of the trapezoidal opening 28.

A ventilating fan assembly 12 fits inside the top opening 20. The ventilating fan assembly has a motor mount boss 32 connected to a fan shroud 34 by a race strut 36. A pair of flexible face flange struts (pair of flexible face flange mounting struts) 38 are attached to the fan shroud 34. A plurality of fan blades rotate freely inside the fan shroud 34. At the free end of the pair of flexible face flange mounting struts 38 are a pair of dumbbell flanges (pair of mating buttons) 40. The dumbbell flanges 40 are inserted into the locking holes (pair of keyholes) 30, to hold the fan assembly 12 against the face flange 26 between the lens subframe 14 and the face subframe 16. The fan shroud 34 extends into the trapezoidal opening 28. A foam face buffer covers the face flange and prevents the user from feeling the mating buttons 40 or the fan shroud 34. A foam sleeve 42 fits over an electric motor 44. The foam sleeve 42 isolates the vibration of the motor 44 from the motor mount boss 32. This reduces the noise from the motor 44. The motor 44 with the foam sleeve fits inside the motor mount boss 32. In one embodiment the motor is a coreless fan motor. The coreless fan motor can be an electronic commutator motor having three windings.

A cover 46 having an opening 48 for the fan exhaust vent fits over the top open portion 20. In one embodiment the cover (air impermeable cover) 46 is made of an air impermeable material such as a closed cell foam. An air permeable foam (fan exhaust vent foam) 50 fits over the exhaust vent of the high pressure side of the fan. An air permeable foam is used to cover the cheek vents 22. The sports goggle 10 generally includes a head strap attached to the ends of the frame.

Figure 2:
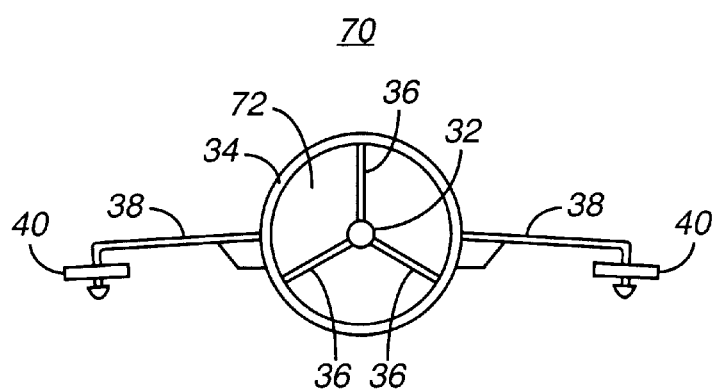
FIG. 2 is a top view of an embodiment of a fan housing according to the invention.

FIG. 2 is a top view of an embodiment of a fan housing 70 according to the invention. The drawing shows an effective fan area 72 as the area between the motor mount boss 32 and the fan shroud 34. The effective fan area 72 is important in determining the air flow capacity of the fan. Smaller effective fan areas require that the fan operate at a faster speed to have the same air flow capacity, however as the fan speed is increased, the motor noise increases. Above a fan tip blade speed of about seven meters per second the noise becomes very noticeable to a user. Below about four meters per second the fan noise is essentially inaudible. The fan blade tip speed is a function of the fan diameter and the operating speed of the motor. The effective fan area is also limited by the size of the top opening in the standard sports goggle. Based on these constraints, it has been found that a minimum effective area is about 180 square millimeters.

Figure 3:
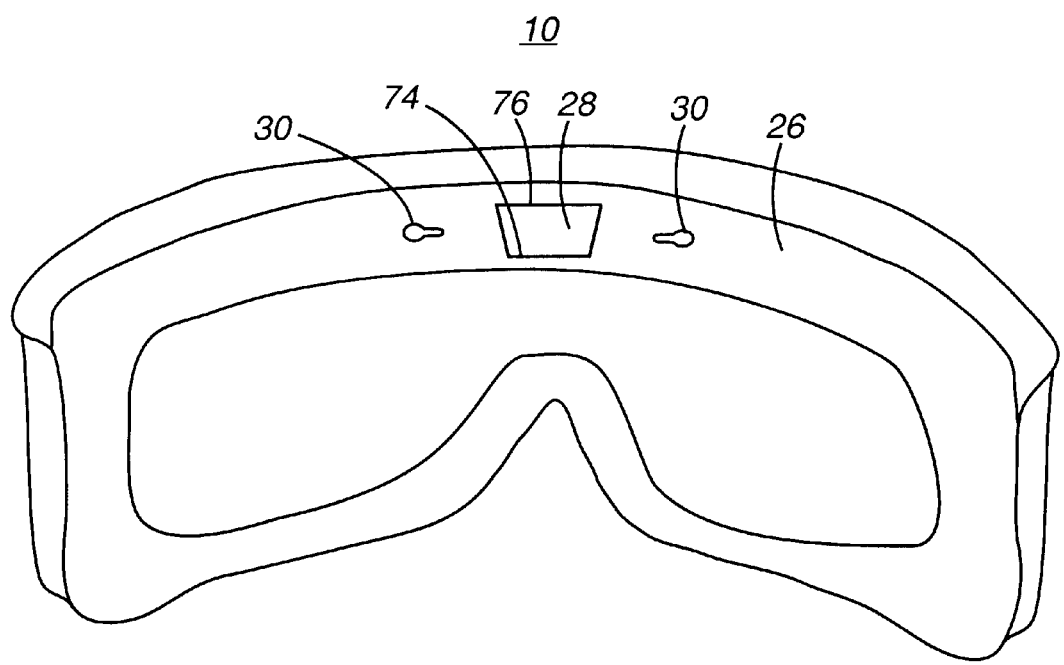
FIG. 3 is a back view of an embodiment of a sports goggle according to the invention.

FIG. 3 is a back view of an embodiment of a sports goggle 10 according to the invention. This view shows the face flange 26 of the face subframe 16. The drawing shows the trapezoidal opening 28 into which the fan shroud 34 partially slides. The trapezoidal opening 28 provides a seat for the fan shroud 34. The smaller side 74 of the trapezoidal opening 28 is sized so that the shroud 34 just sits on the ledge of the opening and cannot protrude beyond this point. The larger side 76 is designed to provide extra space for the fan assembly. It is not as important if the larger side 76 slightly overlaps the effective area of the fan, since the larger side 76 is on the exhaust side of the fan. However any overlap of the effective area on the short side 74 would block the (low pressure) intake side of the fan and impact the air flow capacity of the fan. The locking holes (mounting holes, keyholes) 30 are designed so that the face flange 26 must be deformed to allow the mating buttons to fit through larger part of the hole 30. When the face flange 26 is no longer deformed the buttons 40 slide into the narrow curve of the holes 30. In this way the fan assembly is attached to the face flange 26. As will be apparent to those skilled in the art a variety of different mounting mechanisms could also be used.

The fan is designed so that air is pulled through the cheek vents 22 and exhausted out of the top brim 20. The top cover 46 is purposely designed to prevent air from entering the top opening 20 as the user moves. In fact as the user moves the air capacity of the fan is reduced. This keeps the lens 24 from becoming excessively cooled as the user moves and therefore lowers the likelihood that the lens will fog once the user stops moving.

Thus there has been described a sports goggle with a fan assembly that can be used with a variety of models of sports goggles. The mounting method takes advantage of the face flange that exists on most sports goggles. The mounting method does not require a custom and inflexible mounting assembly. The flexible flanges allow the face flange to conform to user's head. The motor is designed to operate effectively at a speed that is hardly noticeable to a user.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. A sports goggle comprising:

a lens subframe;

a face subframe having a face flange, the face subframe connected to the lens subframe by a plurality of spacer struts, the plurality of spacer struts forming a top brim, the face flange having a forehead portion; and a ventilating fan assembly having a pair of flexible face flange struts attaching to the forehead portion of the face flange and designed to exhaust air through a fan exhaust vent in the top brim.

2. The sports goggle of claim 1, further including a cover over the top brim except for the fan exhaust vent.

3. The sports goggle of claim 2, further including an air permeable foam covering the fan exhaust vent.

4. The sports goggle of claim 3, further including an air permeable foam covering a cheek vent formed between the lens subframe and the face subframe.

5. The sports goggle of claim 2, wherein the cover is made of a closed cell foam.

6. The sports goggle of claim 1, wherein the ventilating fan assembly further includes a coreless motor.

7. The sports goggle of claim 1, wherein the ventilating fan assembly has an effective fan area of at least 180 square millimeters.

8. A sports goggle comprising:

a lens subframe;

a face subframe attached to the lens subframe by a plurality of spacer struts, the plurality of spacer struts forming a top open portion, a pair of cheek open portions, the face subframe having a face flange conforming to a user's face, the face flange having a trapezoidal opening in a forehead portion and a pair of locking holes on either side of the trapezoidal opening; and a ventilating fan assembly having a pair of flexible face flange struts with a pair of mating buttons at a free ends of the pair of flexible face flange struts, the mating buttons engaging the pair of locking holes.

9. The sports goggle of claim 8, wherein a fan shroud of the ventilating fan assembly partially fits inside the trapezoidal opening.

10. The sports goggle of claim 8, further including an air impermeable cover having an opening for a fan exhaust vent and fitting over the top open portion.

11. The sports goggle of claim 8, further including a coreless motor mounting in the fan ventilating assembly, the coreless motor designed to pull air in through the cheek open portions and to exhaust the air through the fan exhaust vent.

* * * * *